US010695042B2

(12) United States Patent
Marchand

(10) Patent No.: US 10,695,042 B2
(45) Date of Patent: Jun. 30, 2020

(54) MARCHAND SALPINGECTOMY—A LAPAROSCOPIC SURGICAL TECHNIQUE

(71) Applicant: Greg J. Marchand, Mesa, AZ (US)

(72) Inventor: Greg J. Marchand, Mesa, AZ (US)

(73) Assignee: Marchand Institute for Minimally Invasive Surgery, Mesa, AZ (US)

( * ) Notice: Subject to any disclaimer, the term of this patent is extended or adjusted under 35 U.S.C. 154(b) by 155 days.

(21) Appl. No.: 15/786,602

(22) Filed: Oct. 18, 2017

(65) Prior Publication Data

US 2019/0110787 A1 Apr. 18, 2019

(51) Int. Cl.
| | | |
|---|---|---|
| A61B 17/02 | (2006.01) | |
| A61B 17/34 | (2006.01) | |
| A61B 17/42 | (2006.01) | |
| A61B 17/29 | (2006.01) | |
| A61B 18/14 | (2006.01) | |
| A61B 18/00 | (2006.01) | |

(52) U.S. Cl.
CPC ...... *A61B 17/0218* (2013.01); *A61B 17/3417* (2013.01); *A61B 17/42* (2013.01); *A61B 17/29* (2013.01); *A61B 17/3421* (2013.01); *A61B 18/14* (2013.01); *A61B 18/1482* (2013.01); *A61B 2017/4233* (2013.01); *A61B 2018/00601* (2013.01)

(58) Field of Classification Search
CPC ............ A61B 17/0218; A61B 17/0281; A61B 2017/00637
See application file for complete search history.

(56) References Cited

U.S. PATENT DOCUMENTS

| | | | | |
|---|---|---|---|---|
| 5,227,736 A | * | 7/1993 | Tucker | H03F 1/3252 327/100 |
| 5,921,993 A | * | 7/1999 | Yoon | A61B 17/12013 606/139 |
| 2010/0185053 A1 | * | 7/2010 | Hagen | A61B 1/00154 600/114 |

* cited by examiner

*Primary Examiner* — Anu Ramana

(57) ABSTRACT

The Marchand Salpingectomy is a fast, safe and minimally invasive procedure for removal of the fallopian tubes. The procedure involves minimal blood loss and gives the patient the benefit of permanent sterility as well as a decreased lifetime incidence of ovarian cancer. The procedure relies on two novel aspects of the technique which make the surgery significantly different than any surgery previously described as well as extremely minimally invasive.

3 Claims, 3 Drawing Sheets

MARCHAND SALPINGECTOMY—A LAPAROSCOPIC SURGICAL TECHNIQUE

CROSS-REFERENCE TO RELATED APPLICATION

Original Non-Provisional Application

BACKGROUND

Current surgical techniques exist to remove the fallopian tubes and known laparoscopic techniques include removal of the fallopian tubes using small holes. The surgical technique presented herein, relates to the technical fields of gynecology and laparoscopy surgery, and specifically, removal of the fallopian tubes.

This new technique, includes unique, previously undescribed characteristics which incorporates the unique aspect of the high placement of a 5 mm port which resides through an incision that is below the pubic hairline, the unique aspect of removing the fallopian tubes by plunging each tube individually through an 11 mm port using the 5 mm port and a 5 mm blunt grasper, and represents a new surgical process that is unique and has the potential to decrease operative time while increasing patient safety.

The Marchand Salpingectomy is a fast, safe and minimally invasive procedure for removal of the fallopian tubes. The procedure involves minimal blood loss and gives the patient the benefit of permanent sterility as well as a decreased lifetime incidence of ovarian cancer. The procedure relies on two novel aspects of the technique which make the surgery significantly different than any surgery previously described as well as extremely minimally invasive.

SUMMARY OF THE TECHNIQUE

Known laparoscopic techniques include removal of the fallopian tubes using small holes. The disclosed technique, however, uses an 11 mm and 5 mm laparoscopic trocar port in order to remove the fallopian tubes in a very fast and cosmetic manner with minimal blood loss.

The procedure includes placing an incision of approximately 5 mm approximately 3 cm above the pubic symphysis in the midline, below the pubic hairline. The skin edge is pulled up approximately 3 more cm while placing the abdominal trocar. This gives the unique advantage of a trocar site higher on the abdomen without the disadvantage of a scar.

The procedure also includes placing a small incision and then an 11 mm trocar at the bottom of the umbilicus into the abdominal cavity. A blunt bipolar laparoscopic device using bipolar energy is utilized in order to divide each fallopian tube from their origin at the uterus. The dissection is carried out the entire length of each fallopian through the broad ligament. This is repeated on both sides until both fallopian tubes are free in the abdominal cavity. This technique includes the unique aspect of removing the fallopian tubes by plunging each tube individually through the 11 mm trocar port using the 5 mm port and a 5 mm blunt grasper.

DETAILED DESCRIPTION

Known laparoscopic techniques include removal of the fallopian tubes using small holes. The technique disclosed herein uses an 11 mm and 5 mm laparoscopic trocar port in order to remove the fallopian tubes in a very fast and cosmetic manner with minimal blood loss.

Figure 1A:
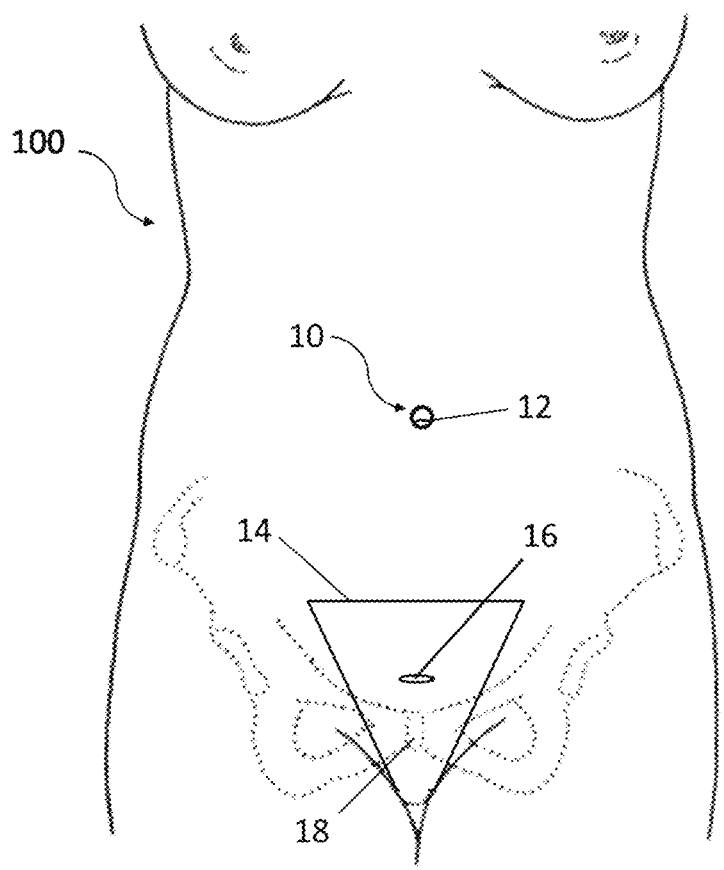
FIG. 1A: Drawing which illustrates the entry points into the abdominal cavity.
Figure 1B:
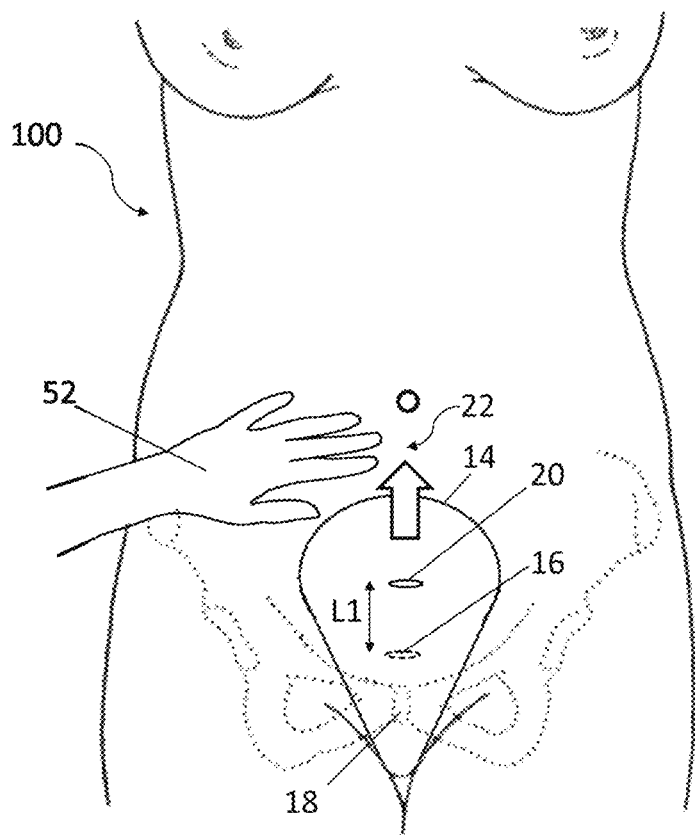
FIG. 1B: Drawing which shows the action of pulling the skin edge cephalad to facilitate a higher entry into the abdominal cavity despite a lower incision below the pubic hairline.

The technique begins the patient 100 prepped, draped, and under general anesthesia as is common for laparoscopic techniques. Next, the procedure continues with placing a small first incision 12 and then an 11 mm trocar 46 at the bottom of the umbilicus 10 into the abdominal cavity 38, and then placing a second incision 16 of approximately 5 mm approximately 3 cm above the pubic symphysis 18 in the midline or medial plane of the body, below the pubic hairline 14. As shown in FIG. 1B, the skin edge 22 is manually pulled approximately 3 cm L1 by a member of the surgical team 52, causing the second incision 16 to be pulled cephalad while placing the abdominal trocar 44. This gives the unique advantage of a trocar site 20 higher on the abdomen without the disadvantage of a scar. Because the second incision 16 was originally below the pubic hairline 14, the incision 16 will ultimately return to this position following the surgery.

Figure 2A:
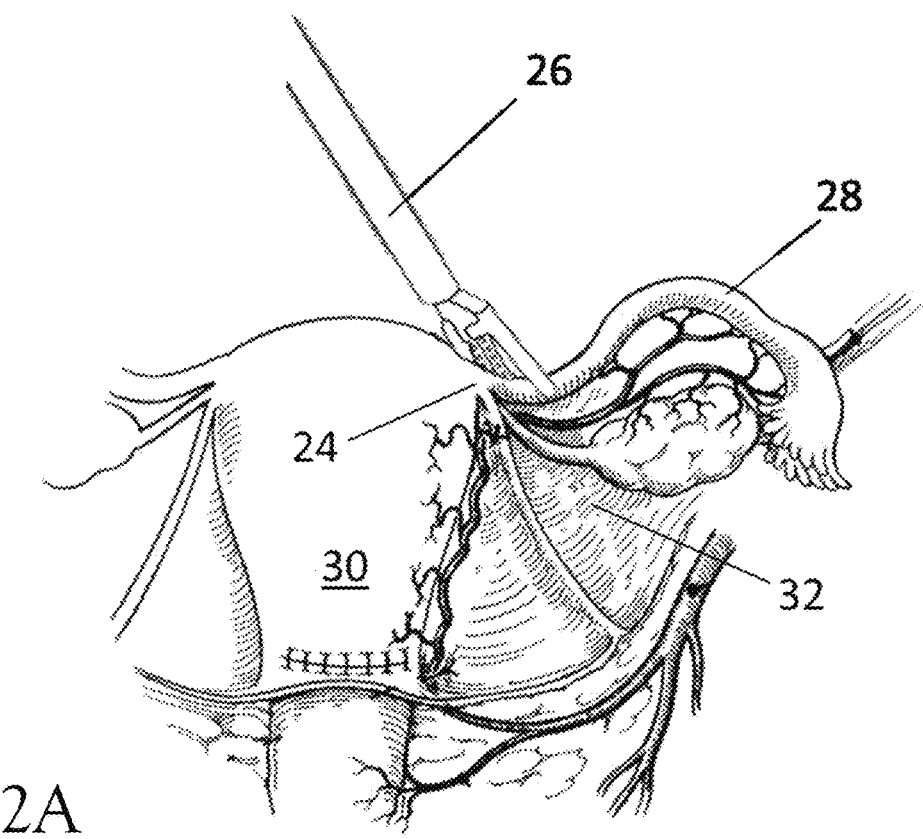
FIG. 2A: Drawing which shows the dissection of the fallopian tubes using a 5 mm bipolar device.
Figure 2B:
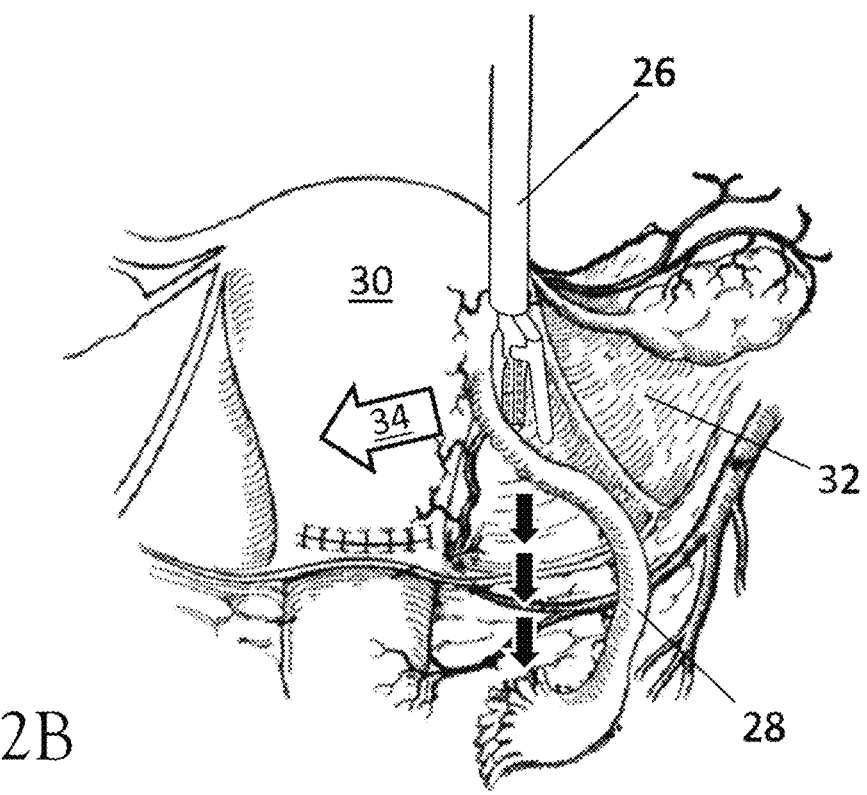
FIG. 2B: Drawing which shows the path of the 5 mm bipolar device and forces applied during the dissection of the fallopian tubes from the broad ligament.

Next, a blunt bipolar laparoscopic device 26 using bipolar energy is utilized in order to divide the fallopian tube 28 from the fallopian tube's origin 24 at the uterus 30 as shown in FIG. 2A. The dissection is carried out the entire length of each fallopian tube 28 through the broad ligament 32 as shown in FIG. 2B. During the dissection, medial traction 34 is enacted by the bipolar laparoscopic device 26. The incision plane is kept as medial in the abdominal cavity 38 as possible in order to avoid any possibility of damage to lateral structures. This process is repeated on both sides until both fallopian tubes 28 are free in the abdominal cavity 38.

Figure 3A:
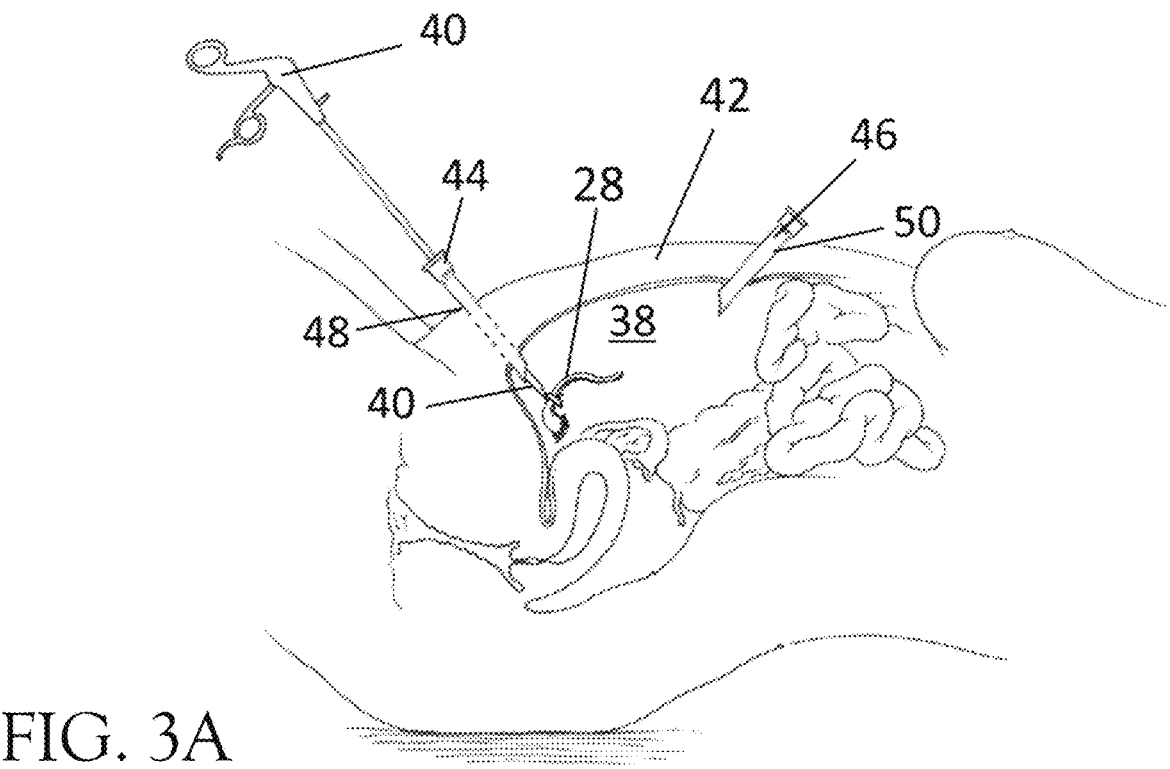
FIG. 3A: Drawing showing the removal of the fallopian tubes using a 5 mm grasper inside the abdominal cavity.
Figure 3B:
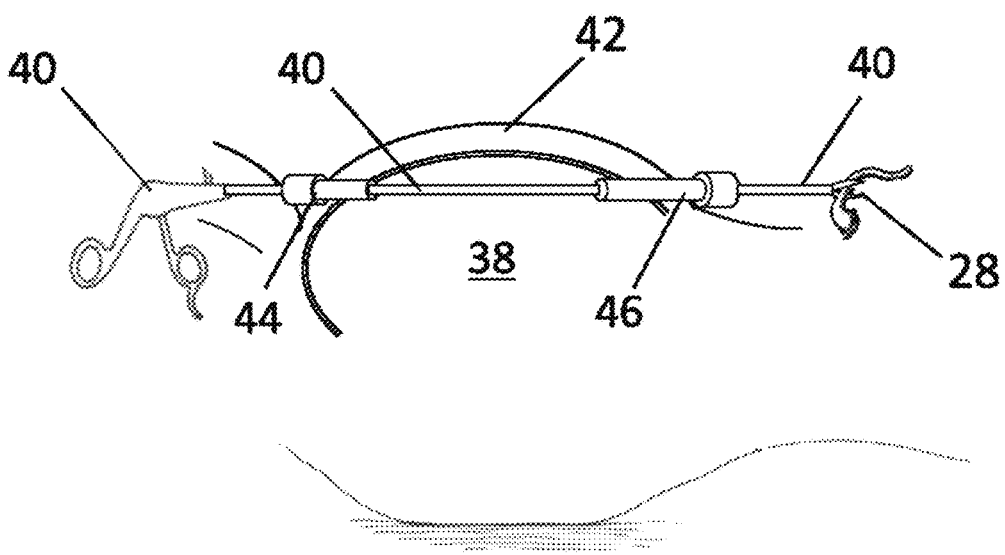
FIG. 3B: Drawing which shows the removal of the fallopian tubes using one port to plunge the fallopian tube through the other larger port.

The next important and unique aspect of the technique is the removal of the fallopian tubes 28 from the abdominal cavity 38. FIG. 3A shows the free fallopian tube 28 being seized within the abdominal cavity 38 by a 5 mm grasper 40 which is utilized through the 5 mm trocar 44. FIG. 3B shows plunging the fallopian tube 28 through the 11 mm trocar 46 port using the 5 mm grasper 40. Each fallopian tube 28 is removed in this manner.

Following this, 30 cc of Marcaine is injected into the abdominal cavity to help with postoperative pain, and the fascia for the 11 mm incision 12 is closed with a vicryl. The skin for both the first incision 12 and second incision 16 is closed with glue and covered with band-aids. The surgery is then considered complete.

As presented, this technique includes the unique aspect of the high placement of the 5 mm trocar port 44 which resides through an incision 16 that is below the pubic hairline 14, the unique aspect of removing the fallopian tubes 28 by plunging each tube individually through the 11 mm trocar port 46 using the 5 mm port 44 and a 5 mm blunt grasper 40, and represents a new surgical process that is unique and has the potential to decrease operative time while increasing patient safety.

The invention claimed is:

1. A method to introduce a 5 mm trocar port through an incision that is below the pubic hairline of a patient comprising the steps of:
    creating an incision at a point located near the medial plane of the patient between the pubic symphysis and the anterior edge of the pubic hairline; said incision defined by a skin edge whereby applying pressure cephalad on the external surface of the patient's abdomen causes the skin edge of said incision to traverse cephalad a distance of approximately 3 cm to a high placement location and;
    introducing a distal end of a 5 mm trocar into the abdominal cavity of the patient through the incision located at the high placement location.

2. A method of dissecting a fallopian tube from a patient's uterus and removing said fallopian tube from the patient's abdominal cavity comprising the steps of:
    introducing a distal end of a first trocar into the abdominal cavity of a patient through a first incision, wherein the first incision is located at the bottom of the umbilicus;
    creating a second incision at a point located near the medial plane of the patient between the pubic symphysis and the anterior edge of the pubic hairline;
    applying pressure on the external surface of the patient's abdomen to cause said second incision to traverse cephalad a distance of approximately 3 cm to a high placement location;
    introducing a distal end of a second trocar into the abdominal cavity of the patient through the second incision located at the high placement location;
    introducing a distal end of a bipolar laparoscopic device having the capability to perform dissection by utilizing bipolar energy, into the patient's abdominal cavity through a port existing in the second trocar;
    dividing the patient's fallopian tube utilizing the bipolar laparoscopic device from the uterus at a point where said fallopian tube originates at the uterus;
    continuing the dissection of the fallopian tube from the broad ligament of the uterus utilizing the bipolar laparoscopic device while applying medial traction onto the lateral wall of the fallopian tube with said bipolar laparoscopic device until the fallopian tube is free in the abdominal cavity;
    introducing a distal end of a grasping device having a pair of opposing jaws into the patient's abdominal cavity through the second trocar and seizing the free fallopian tube from the abdominal cavity within said jaws; and
    passing the distal end of said grasping device holding said free fallopian tube from the abdominal cavity through the first trocar such that the jaws of said grasping device and free fallopian tube are presented outside of the patient's body.

3. A method of dissecting a pair of fallopian tubes from a patient's uterus and removing said fallopian tubes from the patient's abdominal cavity comprising the steps of:
    introducing a distal end of a first trocar into the abdominal cavity of a patient through a first incision, wherein the first incision is located at the bottom of the umbilicus;
    creating a second incision at a point located near the medial plane of the patient between the pubic symphysis and the anterior edge of the pubic hairline and introducing a distal end of a second trocar into the abdominal cavity of the patient through the second incision;
    introducing a distal end of a bipolar laparoscopic device having the capability to perform dissection by utilizing bipolar energy, into the patient's abdominal cavity through a port existing in the second trocar;
    dividing the patient's first fallopian tube utilizing the bipolar laparoscopic device from the uterus at a point where said first fallopian tube originates at the uterus;
    continuing the dissection of the first fallopian tube from the broad ligament of the uterus utilizing the bipolar laparoscopic device while applying medial traction onto the lateral wall of the first fallopian tube with said bipolar laparoscopic device until the first fallopian tube is free in the abdominal cavity;
    dividing the patient's second fallopian tube utilizing the bipolar laparoscopic device from the uterus at a point where said second fallopian tube originates at the uterus;
    continuing the dissection of the second fallopian tube from the broad ligament of the uterus utilizing the bipolar laparoscopic device while applying medial traction onto the lateral wall of the second fallopian tube with said bipolar laparoscopic device until the second fallopian tube is free in the abdominal cavity;
    introducing the distal end of a grasping device with a pair of opposing jaws into the patient's abdominal cavity through the second trocar and seizing the free first fallopian tube from the abdominal cavity within said jaws and passing the distal end of said grasping device holding said free first fallopian tube from the abdominal cavity through the first trocar such that the jaws of said grasping device and free first fallopian tube are presented outside of the patient's body;
    re-introducing the distal end of the grasping device with opposing jaws into the patient's abdominal cavity through the second trocar and seizing the free second fallopian tube from the abdominal cavity within said jaws and passing the distal end of said grasping device holding said free second fallopian tube from the abdominal cavity through the first trocar such that the jaws of said grasping device and free second fallopian tube are presented outside of the patient's body.

\* \* \* \* \*